US00PP32036P2

(12) United States Plant Patent
Hansen

(10) Patent No.: US PP32,036 P2
(45) Date of Patent: Aug. 4, 2020

(54) ***HIBISCUS* PLANT NAMED 'DARK MYSTERY'**

(50) Latin Name: ***Hibiscus* hybrid (L.)**
Varietal Denomination: Dark Mystery

(71) Applicant: Hans A Hansen, Zeeland, MI (US)

(72) Inventor: Hans A Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 2 days.

(21) Appl. No.: 16/501,325

(22) Filed: Mar. 26, 2019

(51) Int. Cl.
*A01H 6/60* (2018.01)
*A01H 5/02* (2018.01)

(52) U.S. Cl.
USPC ..... Plt./257

(58) Field of Classification Search
USPC ..... Plt./257
CPC ..... A01H 5/02; A01H 6/60
See application file for complete search history.

*Primary Examiner* — Annette H Para

(57) ABSTRACT

A new and distinct cultivar of winter-hardy, herbaceous, perennial, hybrid *Hibiscus* plant named 'Dark Mystery' comprising a rounded mound habit of multiple, well-branched, basal stems producing flowers from the bottom to the top of the plant for five to six weeks from late July to early September. Flowers have petals of pale pink to light pink with strong reddish veins radiating toward margin and dark, red, shiny eye set off with column of cream-colored pollen. The foliage is cordate to ovate and deep mahogany-colored.

2 Drawing Sheets

Botanical classification: *Hibiscus* hybrid (L.).
Variety denomination: 'Dark Mystery'.

STATEMENT REGARDING PRIOR DISCLOSURES UNDER 37 CFR 1.77(b)(6)

The first publically released non-enabling description was a photograph and brief description of the new plant was on Feb. 1, 2019 when it was placed on a website operated by Walters Gardens, Inc. The first disclosure, in the form of a sale, was made by Walters Gardens, Inc. on Apr. 1, 2018. Walters Gardens, Inc. obtained the new plant and all information relating thereto, from the inventor. No plants of *Hibiscus* 'Dark Mystery' have been sold, in this country or anywhere in the world, nor has any disclosure of the new plant been made, more than one year prior the filing date of this application, and such sale or disclosure within one year was either derived directly or indirectly from the inventor.

BACKGROUND AND ORIGIN OF THE PLANT

The present invention relates to the new and distinct hardy, herbaceous, *hibiscus* plant, *Hibiscus* 'Dark Mystery' hybridized under direction of the inventor on Aug. 8, 2013 at a wholesale perennial nursery in Zeeland, Mich. The new plant is a hybrid of the complex, unreleased, proprietary hybrid known as E26-101(not patented) times a hybrid of the complex, unreleased, proprietary hybrid known as 11-117-104 (not patented). Into the trial process the new plant was assigned the breeder code labeled 13-45-111. Both parents have a complex mixture of species in them, comprising the species: *moscheutos* and *coccineus*.

*Hibiscus* 'Dark Mystery' was first asexually propagated in late summer of 2016 by sterile shoot-tip tissue culture and later by shoot tip cuttings at the same nursery in Zeeland, Mich. The resultant asexually propagated plants have been found to be stable and true to type in successive generations of asexual reproduction.

BRIEF SUMMARY OF THE PLANT

*Hibiscus* 'Dark Mystery' differs from its parents as well as all other hardy herbaceous *hibiscus* known to the applicant in many traits. The most similar *hibiscus* known to the applicant are 'Perfect Storm' U.S. Plant Pat. No. 27,880, 'Crown Jewels' U.S. Plant Pat. No. 11,857, 'Kopper King' U.S. Plant Pat. No. 10,793, 'Summer Storm' U.S. Plant Pat. No. 20,443, 'Holy Grail' U.S. Plant patent application Ser. No. 16/350,349 and 'Mocha Moon' U.S. Plant Pat. No. 27,837. 'Perfect Storm' has flower petals are that are more cupped, and the foliage is more tri-lobed than that of the new plant and the habit is shorter. 'Crown Jewels' has smaller habit and the foliage is tri-lobed without the intense mahogany coloration. 'Kopper King' has foliage that is larger, tri-lobed, more medium green with weaker dark mahogany coloration, and the habit is slightly taller and more upright with less branching than the new plant. 'Holy Grail' is similar in foliage, with slightly shorter habit, and the flowers are deep reddish-colored. 'Mocha Moon' has more cupped flowers with less pinkish color and reddish veins in the outer petal portion, the petals are more folded in the inner edge and less puckered and the foliage is more frequently tri-lobed. 'Perfect Storm' has a taller more open habit, mostly tri-lobed foliage and the flower has a deeper red center eye.

The female parent, E26-101, is taller and more upright in habit, the foliage tri-lobed and color was not as deep mahogany, and the flower is moderate red with deeper burgundy eye and pollen color of greyed-yellow. The male parent, 11-117-104, is more compact in habit, and the flowers are near white with a lustrous bright-red eye zone and veins of bright-red and marginal red tinting on the distal portion, and the foliage is similarly colored deep mahogany but deeply-dissected with three to five lobes.

*Hibiscus* 'Dark Mystery' is a unique hardy herbaceous *hibiscus* with the following combined traits:

1. Winter-hardy compact perennial with upright habit of multiple, well-branched, basal stems.
2. Many flat rotate flowers produced from bottom to top of plant.
3. Flowers produced for about five to six weeks beginning mid-summer.
4. Flower petals of pale pink to light pink.
5. Flower has a bright, red, shiny eye zone and strong red veins radiating toward petal margins set off with column of pale yellow pollen.
6. Cordate to ovate foliage strongly colored with deep mahogany.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source and direction may cause the appearance of minor variation in color.

DETAILED BOTANICAL DESCRIPTION

Figure 1:
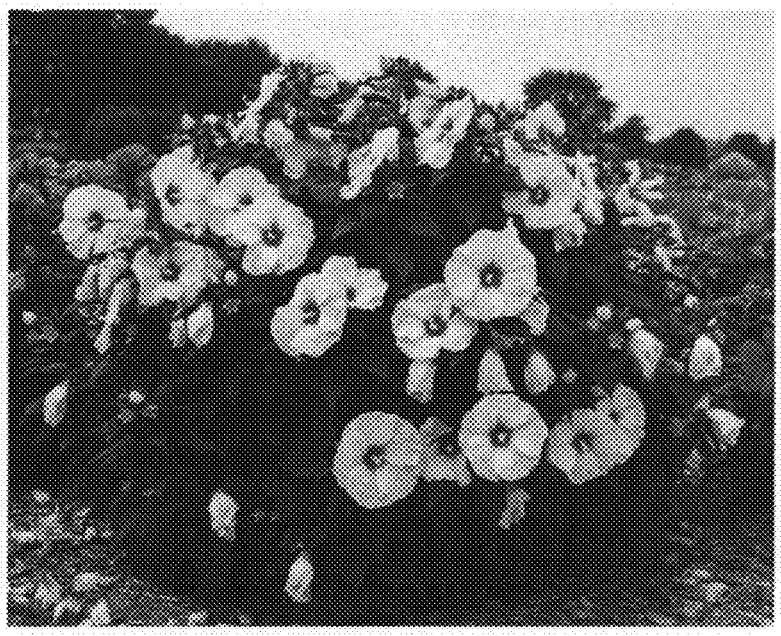
FIG. 1 shows a five-year-old plant in full flower in a trial garden.
Figure 2:
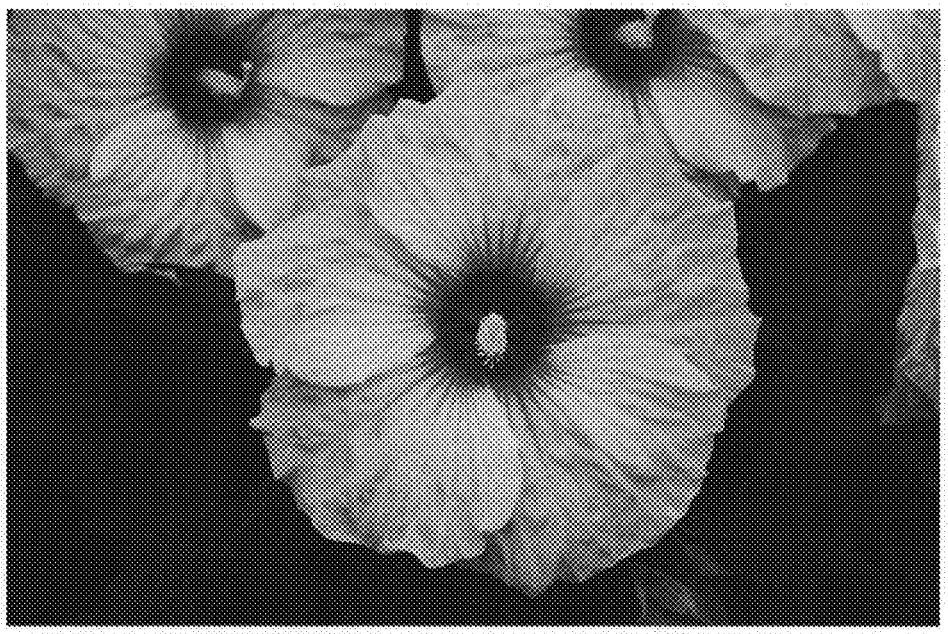
FIG. 2 shows a close-up of the flower and bud.
Figure 3:
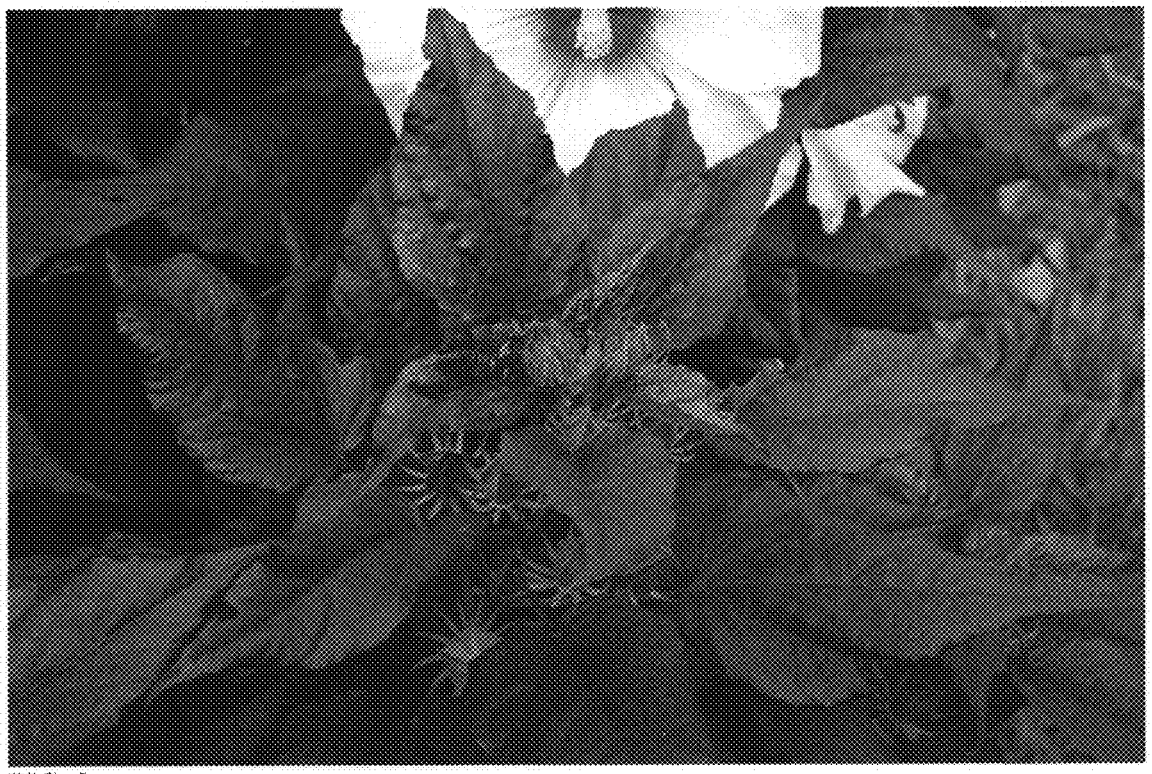
FIG. 3 shows the terminal foliage with stem and young flower buds.

The following descriptions and color references are based on the 2001 edition of The Royal Horticultural Society Colour Chart except where common dictionary terms are used. The new plant, *Hibiscus* 'Dark Mystery', has not been observed under all possible environments. The phenotype may vary slightly with different environmental conditions, such as temperature, light, fertility, moisture and maturity levels, but without any change in the genotype. The following observations and size descriptions are of five-year-old plants in the loamy-sand, open-field full-sun trials of a nursery in Zeeland, Mich. with supplemental fertilizer and water as needed. The plants are of natural habit and were not treated with plant growth regulators, nor were they pinched at any time in the growth year.

Parentage: The female or seed parent is the unreleased, proprietary *hibiscus* known by the breeder code E26-101, the male or pollen parent is the unreleased, proprietary *hibiscus* known by the breeder code 11-117-104.

Propagation:

*Method.*—Shoot tip cuttings and sterile shoot-tip plant tissue culture division.

*Time to initiate roots from tissue culture.*—About two weeks.

*Rooting habit.*—Normal, branching, developing thick to about 2.8 cm diameter, fleshy; root color creamy yellow nearest RHS 161D depending on soil type.

*Crop time.*—Under normal summer growing conditions 12 to 16 weeks to flower in a four-liter container from cutting; plant vigor very good.

Plant description:

*Plant habit.*—Winter-hardy herbaceous perennial with about 78 thick, upright, heavily-branched stems producing an upright spreading mound to about 160.0 cm tall and about 198.0 cm wide.

*Stem.*—Cylindrical, glabrous, glaucous; to about 150.0 cm tall and about 21.0 mm diameter at base, average about 105.0 cm tall and about 18.0 mm diameter at base.

*Stem color.*—Nearest RHS 138A with light blushing of nearest RHS N186A.

*Lateral branches.*—To 6 per stem, average about 4 per stem; cylindrical, glabrous, glaucous; to about 44.0 cm long and 6.0 mm diameter at base, smaller distally.

*Lateral branch color.*—Nearest RHS 138A with light blushing of nearest RHS N186A.

*Internode.*—About 8 nodes per stem below branches; average internode length about 3.5 cm of unpinched plant.

*Internode color.*—Same as surrounding stem.

Foliage description: Typically ovate to cordate; alternate; apex narrowly acute; base rounded to nearly cordate; margin coarsely and irregularly dentate; glabrous abaxial and adaxial; adaxial surface lustrous when expanding, slightly lustrous when mature, abaxial surface matte; leaf blades to about 13.5 cm long and about 8.5 cm across, average blade size 11.5 cm long and 7.5 cm wide; no fragrance detected.

*Foliage color.*—Young expanding leaves — adaxial between RHS N186B and RHS N186C, abaxial nearest blend between RHS 147B and RHS N138C with irregular blushing typically around leaf margins nearest RHS 187B; mature leaves — adaxial between RHS N186A and RHS N186B in high light exposure and nearest RHS 137A with undertones of nearest RHS N186B, abaxial nearest RHS 147B.

*Veins.*—Palmate; lustrous; costate on abaxial.

*Vein color.*—Young adaxial veins nearest RHS N186C with midrib nearest RHS 186A, abaxial veins nearest RHS 185C and midrib nearest RHS 185B; mature adaxial nearest RHS 183D to RHS 187B and abaxial midrib nearest RHS N186C proximally and distally nearest RHS 185B, veins nearest RHS 185D.

*Petioles.*—Mostly cylindrical, proximally slightly applanate on adaxial side near base; glaucous; glabrous; to about 8.0 cm long and 3.0 mm diameter at base, average size about 6.5 cm long and 2.5 mm wide at base.

*Petiole color.*—Nearest blend between RHS 187C and RHS 184A.

Flower description: Complete; actinomophic; mostly outward facing; rotate; lasting up to two days on plant; to about 21.5 cm across and mostly flattened petals with column extending 6.8 cm long, decreasing distally.

*Buds one day prior to anthesis.*—Ellipsoidal with rounded apex and bluntly rounded base; sepals adpressed to petals; about 7.0 cm long and about 4.8 cm diameter in middle.

*Bud seven days prior to anthesis, with petals still enveloped in calyx.*—Cylindrical with pointed apex and rounded base; carinate at sepals fusion lines; glabrous, glaucous; about 2.7 cm long and about 1.8 cm across.

*Bud color one day prior to anthesis.*—Exposed petal color distally nearest RHS 63C and proximally nearest RHS 56C.

*Bud seven days prior to anthesis.*—Nearest RHS 147C with blushing at carinae nearest RHS 187B.

*Epicalyx.*—Typically 9 to 11 per flower; linear; entire, glabrous, with margin micro ciliate; dull surface abaxial and adaxial; narrowly acute apex and truncate base, distally arcuate toward apex; about 1.7 cm long and about 1.5 mm wide at base.

*Epicalyx color.*—Adaxial nearest RHS 138B proximally and distally nearest RHS 147B with blushing of nearest RHS 187B, abaxial nearest RHS 146A with moderate tinting of nearest RHS 187A.

*Sepals.*—Five, fused in basal 2.0 cm to form star-shaped hypanthium about 6.0 cm across and 3.5 cm deep; acute apex; glabrous; margin entire, edentate; abaxial and adaxial surfaces matte; individually about 3.7 cm long, about 2.0 cm wide at fusion.

*Sepal color.*—Adaxial between RHS 146D and RHS 145A, veins nearest RHS 145B; abaxial nearest RHS 146D, with veins nearest RHS 145A.

*Flowers.*—Solitary, up to 36 per main stem without pinching; nearly flat face; mostly outwardly facing; natural spread to about 21.5 cm across and 6.5 cm deep from stigma to base of calyx; smaller in later season.

*Flower lastingness.*—Persist for one to two days; effective for five to six weeks beginning late July.

*Flower fragrance.*—None detectable.

*Petals.*—Five; microscopically puberulent abaxial and adaxial, glabrous eye; adnate to the androecium to form a column, imbricate to about 25% overlapping at widest part (petals overlapping 25% to the petals on either side); palmately veined, primary veins impressed on adaxial and slightly costate abaxial; surface slightly dimpled; rounded with distinct claw and limb; margins: entire, edentate; apex rounded; base short claw-like.

*Petal size.*—Average about 10.0 cm across and about 10.0 cm long, claw base about 7.5 mm across (smaller in later part of flowering season).

*Petal color.*—Adaxial blend between RHS N155B and RHS 62D in cooler conditions and nearest RHS N155B in warmer conditions, with darker eye blend between RHS 187D and RHS 53A and veins of between RHS 53B and RHS 187D radiating from eye to about three-fourths of the way to the margin; abaxial basal nearest RHS NN155D with blush of nearest RHS 63D in distal 15 to 20 mm.

*Flower lastingness.*—One to two days.

*Gynoecium.*—Single; partially enclosed in column. Column: glabrous and lustrous, except base micro-puberulent; about 5.0 cm long and about 8.0 mm across at base; with pistil exserted about 12.0 mm. Column color: nearest RHS NN155C. Style: micro-puberulent in region exserted above column; about 6.0 cm long, penta-furcate in about distal 8.0 mm; branch diameter about 1.2 mm; color nearest RHS NN155C. Stigma: typically five; flattened globose, puberulent, about 2.5 mm in diameter and 2.0 mm tall; color nearest RHS 155D. Ovary: superior, semi-globose, rounded to broadly acute apex and flat truncate base; about 8.0 mm across at base and about 5.0 mm tall; acute apex; color between RHS 145C and RHS 145D.

*Androecium.*—Filaments: numerous, about 100; about 4.0 mm long and about 0.2 mm diameter; attached along nearly the entire length of column; color nearest RHS NN155C. Anthers: flattened ellipsoid; dorsifixed; about 2.5 mm long and 2.0 mm across and about 0.8 mm thick; color nearest RHS 155D. Pollen: abundant, globose, less than 0.1 mm long; color nearest RHS 155D.

Pedicel: Cylindrical, glabrous, glaucous; length from base of sepal to abscission point about 1.5 cm long, from abscission point to stem node about 5.5 cm long; about 3.0 mm wide; longer on early flowers and decreasing in distal flowers; color nearest RHS 146C.

Peduncle: Cylindrical, glabrous, glaucous; flowering in the distal 45.0 cm; color nearest RHS 138A with light blushing of nearest RHS N186A.

Fruit: Penta-loculicidal capsule; pubescent along inner septa, glabrous outside; ellipsoidal, cuspidate apex and flattened base; about 26.0 mm long and 20.0 mm diameter; color nearest RHS 200A when mature; up to 72 seeds per fruit.

Seed: Minutely floccose; globose; about 2.4 mm in diameter; color nearest RHS N200A.

Resistance: *Hibiscus* 'Dark Mystery' has not displayed any pest and disease resistance beyond that typical of hardy perennial *hibiscus*. The plant grows best with plenty of moisture. Hardiness at least from USDA zone 4 through 9, and other disease resistance is typical of that of other hardy *hibiscus* cultivars.

I claim:

1. A new cultivar of hardy herbaceous perennial *Hibiscus* hybrid plant named 'Dark Mystery' as herein illustrated and described.

* * * * *